US00PP11225P

United States Patent [19]

Goldup

[11] Patent Number: Plant 11,225

[45] Date of Patent: Feb. 15, 2000

[54] HELICHRYSUM PLANT NAMED 'BLUSHING BEAUTY'

[75] Inventor: Peter Goldup, Mt. Evelyn, Australia

[73] Assignee: Outeniqua Nursery, Emerald, Australia

[21] Appl. No.: 08/977,923

[22] Filed: Nov. 24, 1997

[51] Int. Cl.[7] ..... A01H 5/00

[52] U.S. Cl. ..... Plt./359

[58] Field of Search ..... Plt./68.1, 359

[56] References Cited

U.S. PATENT DOCUMENTS

P.P. 9,667 10/1996 Bautista ..... Plt./68.1

*Primary Examiner*—Howard J. Locker
*Assistant Examiner*—Kent L. Bell
*Attorney, Agent, or Firm*—C. A. Whealy

[57] ABSTRACT

A distinct cultivar of Helichrysum plant named 'Blushing Beauty', characterized by its compact growth habit that is initially upright then outwardly spreading; freely branching and bushy, dense growth; numerous long-lasting inflorescences; inflorescences with light yellow involucral bracts with reddish pink apices and light orange disc florets; and resistance to bacterial pathogens common to Helichrysums.

2 Drawing Sheets

The present invention relates to a new and distinct cultivar of Helichrysum plant, botanically known as *Helichrysum bracteatum,* and hereinafter referred to by the cultivar name 'Blushing Beauty'.

The new Helichrysum was discovered by the inventor in a controlled environment in Mt. Evelyn, Victoria, Australia, in early 1990, as a naturally-occurring mutation of the *Helichrysum bracteatum* cultivar 'Diamond Head' (not patented). The new Helichrysum was observed as a single plant in a population of plants of the parent cultivar as it had a different inflorescence color and was more freely branching and more compact. In addition, plants of the new Helichrysum are more resistant to bacterial pathogens common to Helichrysums and have a longer flowering cycle than plants of the parent cultivar 'Diamond Head'.

Asexual reproduction of the new Helichrysum by terminal cuttings taken at Mt. Evelyn, Victoria, Australia, has shown that the unique features of this new Helichrysum are stable and reproduced true to type in successive generations.

The cultivar 'Blushing Beauty' has not been observed under all possible environmental conditions. The phenotype may vary somewhat with variations in environment such as temperature, light intensity, and fertility level, without, however, any variance in genotype.

The following traits have been repeatedly observed and are determined to be the unique characteristics of 'Blushing Beauty'. These characteristics in combination distinguish 'Blushing Beauty' as a new and distinct cultivar:

1. Compact growth habit that is initially upright then outwardly spreading.
2. Freely branching and bushy, dense growth.
3. Numerous inflorescences that last for at least five weeks.
4. Inflorescences with light yellow involucral bracts with reddish pink apices and light orange disc florets.
5. Resistance to bacterial pathogens common to Helichrysums.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical potted plant of the cultivar 'Blushing Beauty'.

The photograph on the second sheet comprises a close-up view of typical inflorescences of a plant of the cultivar 'Blushing Beauty'. Flower and foliage colors in the photographs may appear different than the actual colors due to light reflectance.

DETAILED BOTANICAL DESCRIPTION

The following observations and measurements describe plants grown during the spring and summer in Encinitas, Calif. under full sun with day and night temperatures averaging 24° and 16° C., respectively. Color references are made to The Royal Horticultural Society Colour Chart except where general terms of ordinary dictionary significance are used.

Botanical classification: *Helichrysum bracteatum* cultivar 'Blushing Beauty'.

Parentage: Naturally-occurring mutation of the *Helichrysum bracteatum* cultivar 'Diamond Head' (not patented).

Propagation:

*Type.*—By cuttings.

*Time to initiate roots.*—12 to 15 days at temperatures of 20° C.

*Time to develop roots.*—21 to 25 days at temperatures of 20° C.

*Rooting habit.*—Vigorous, thick and fleshy.

Plant description:

*Form.*—Initially upright then outwardly spreading, almost pendulous, herbaceous annual, may be perennial in warm climates.

*Branching habit.*—Freely branching, very dense and bushy.

*Plant height.*—About 24 cm.

*Plant diameter.*—About 70 cm.

*Vigor.*—Moderately vigorous.

*Lateral stem description.*—Internode length: About 1.5 cm. Diameter: About 4 mm. Texture: Short white hairs, slightly pubescent. Color: 144A/146A.

*Foliage description.*—Leaves single, alternate and generally symmetrical. Foliage durable. Length: About 11 cm. Width: About 1 cm. Shape: Linear, acuminate apex and sessile. Margin: Entire, ciliate. Texture: Short trichomes on upper surface, rough. Color: Young leaves, upper surface: 147A. Young leaves, lower surface: 147B. Mature leaves, upper surface: 147A. Mature leaves, lower surface: 147B. Venation, upper surface: 147A. Venation, lower surface: 146A, prominent midvein.

Flower description:

*Flower type and habit.*—Single daisy-type composite inflorescence form. Involucral bracts and disc florets arranged acropetally on a capitulum. Inflorescences persistent. Inflorescences orientated perpendicular to stem.

*Quantity of inflorescences.*—Freely flowering with numerous inflorescences per plant. Inflorescences formed at terminals with one per terminal.

*Natural flowering season.*—Natural flowering season is spring to early fall. Plants flower continuously during this period.

*Fragrance.*—Very faint.

*Inflorescence diameter.*—About 4.5 cm.

*Inflorescence depth* (*height*).—About 1.3 cm.

*Receptacle diameter.*—About 1.9 cm.

*Receptacle depth* (*height*).—About 4 mm.

*Involucral bracts.*—Appearance: Straw-like, tough, dry. Aspect: Flat to slightly cupped. Quantity: At least 100 per inflorescence. Shape: Subulate, narrow triangle. Apex: Acute. Base: Truncate, involucral bracts bent at an acute angle at base. Margin: Entire. Length: About 1 cm with green base of 5 mm. Width: About 5 mm. Color: When opening, upper surface: 8D, reddish pink apices. When opening, lower surface: 8D, reddish pink apices. Mature, upper surface: 4C, reddish brown apices. Mature, lower surface: 8D, reddish brown apices.

*Disc florets.*—Shape: Tubular, fluted at apex and heavily whiskered at base. Diameter of disc: About 2.1 cm. Disc floret length: About 1.2 cm. Disc floret width: About 1 mm. Color: Immature: 154B/154C to 3C, with white base. Mature: 23A with white base. Number of disc florets per inflorescence: Typically more than 100.

*Sepals.*—Shape: Linear with acute apex. Margin: Entire. Color: 147A.

*Peduncle.*—Length: 11 cm. Strength: Strong, but flexible and wiry. Texture: Short trichomes. Color: 144A/146A.

*Flower bud.*—Shape: Conical. Length: About 1.8 cm. Diameter: About 1.4 cm. Color: 8D.

*Androecium.*—Anther color: 23A. Pollen color: 23A. Amount of pollen: Abundant.

*Gynoecium.*—Present.

Disease resistance: The new Helichrysum has been observed to be more resistant to bacterial pathogens common to Helichrysums.

Seed production: Seed production has not been observed.

It is claimed:

1. A new and distinct cultivar of Helichrysum plant named 'Blushing Beauty', as illustrated and described.

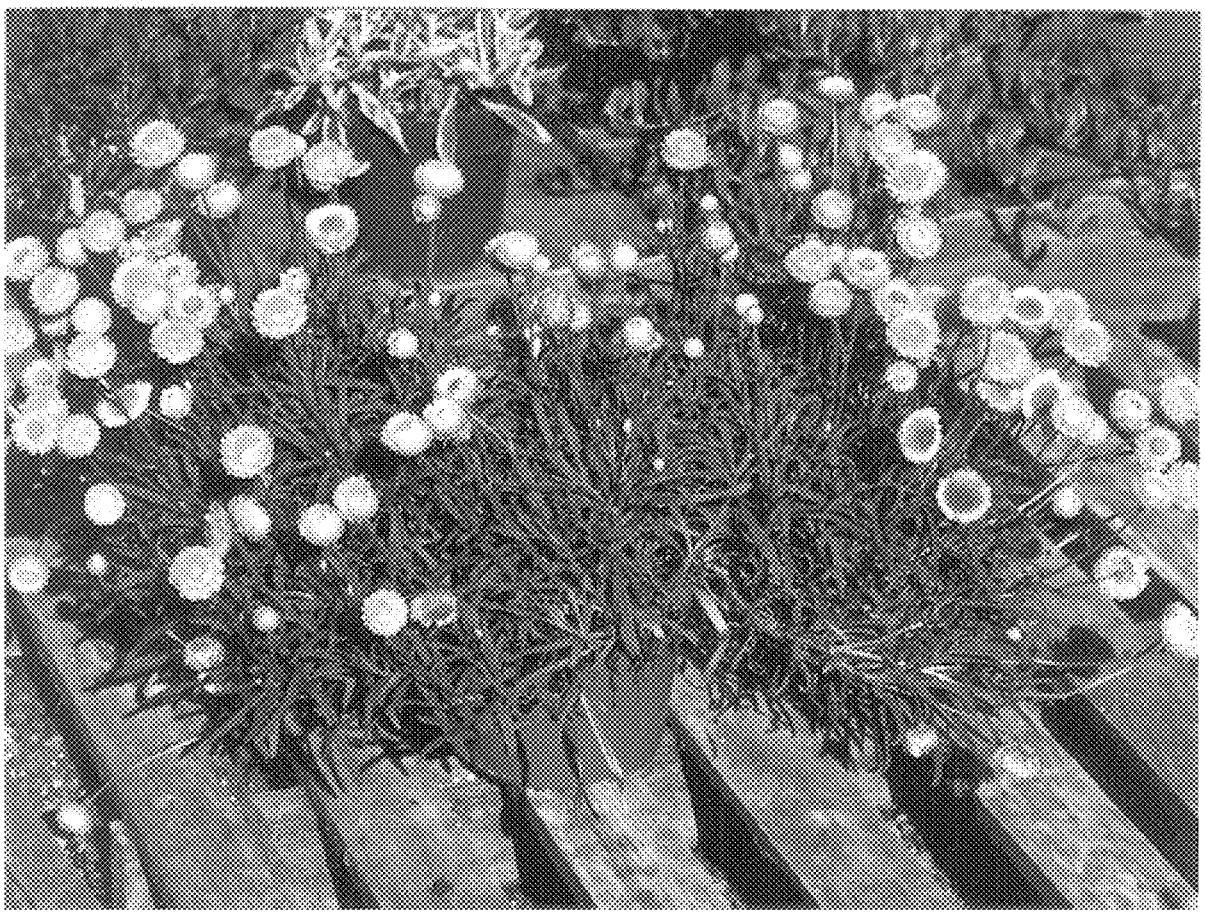

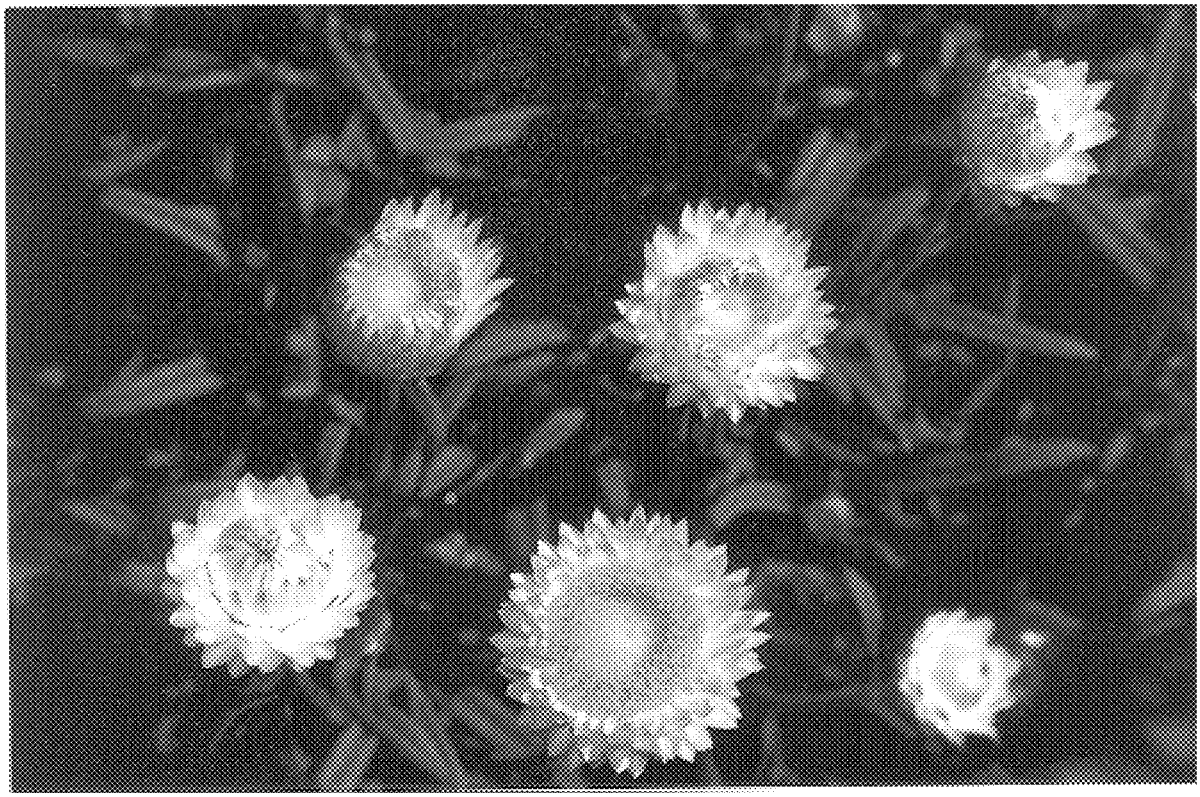

* * * * *